United States Patent [19]

Alpert

[11] Patent Number: 4,517,241

[45] Date of Patent: May 14, 1985

[54] CHROMATOGRAPHIC SUPPORT MATERIAL

[76] Inventor: Andrew J. Alpert, 4417 Darsey, Bellaire, Tex. 77401

[21] Appl. No.: 446,391

[22] Filed: Dec. 2, 1982

[51] Int. Cl.$^3$ .................... B01D 15/08; B05D 3/14; G01H 31/08

[52] U.S. Cl. .................... 428/332; 428/404; 428/406; 428/407; 428/435; 428/442; 428/451; 428/473.5; 428/543; 428/702; 55/386; 210/198.2; 210/659; 210/635; 502/401

[58] Field of Search ............ 428/404, 406, 407, 332, 428/473.5, 435, 702, 442, 451; 252/430

[56] References Cited

U.S. PATENT DOCUMENTS

| | | | |
|---|---|---|---|
| 4,029,514 | 6/1977 | Lange | 428/404 X |
| 4,245,005 | 1/1981 | Regnier et al. | 428/420 |
| 4,318,820 | 3/1982 | Malloy et al. | 252/430 X |
| 4,324,681 | 4/1982 | House | 252/430 X |

OTHER PUBLICATIONS

Temperature Effect on the Molecular Weight and the Optical Purity of Anhydropolyaspartic Acid Prepared by Thermal Polycondensation Kokufuta et al., 51 Bull. Chem. Soc. Jap. 1955, (1978).

Synthesis of $\alpha,\beta$-Poly [(2-hydroxyethyl)-DL-Aspartamidel, a New Plasma Expander, Neri et al., 16 J. of Med. Chem. 893, (1973).

The Characterization of Polyaspartic Acid and Some Related Compounds, Vegotsky et al., 80 J.A.C.S. 3361, (1958).

Chemical Studies of Polyaspartic Acids, Kovacs et al., 26 J. Org. Chem. 1084, (1961).

Primary Examiner—Patrick C. Ives
Attorney, Agent, or Firm—Arnold, White & Durkee

[57] ABSTRACT

A support material comprised of a substrate and a coating bound to the substrate made up of a polymer containing succinimide units or derivatives thereof. A method for preparing a support material comprising reacting a polymer containing succinimide units with surface amine groups on a substrate.

43 Claims, 10 Drawing Figures

SICKLE CELL ANEMIA HEMOGLOBIN

| PEAK | IDENTITY |
|---|---|
| a,b | Hb F |
| c,d,f | MINOR Hb S FORMS |
| e | Hb A$_2$ |
| g | Hb S |

ASPARTIC ACID      POLY SUCCINIMIDE

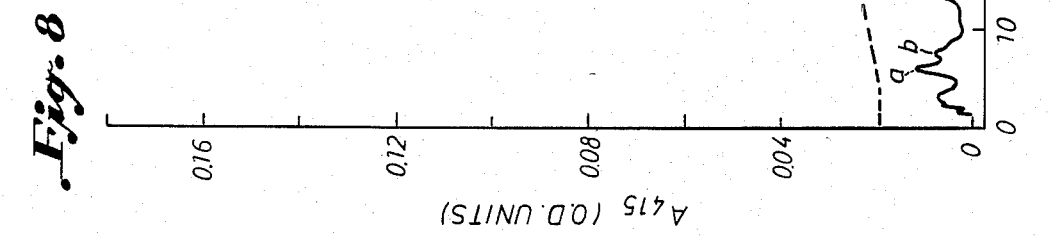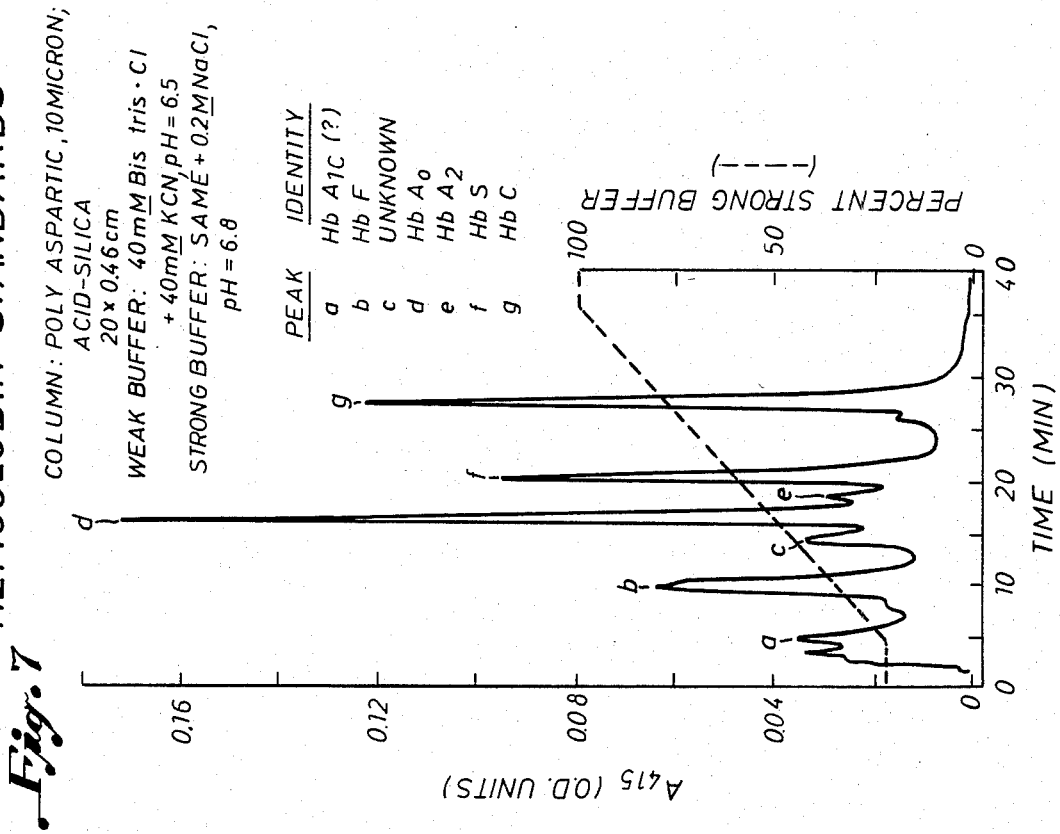

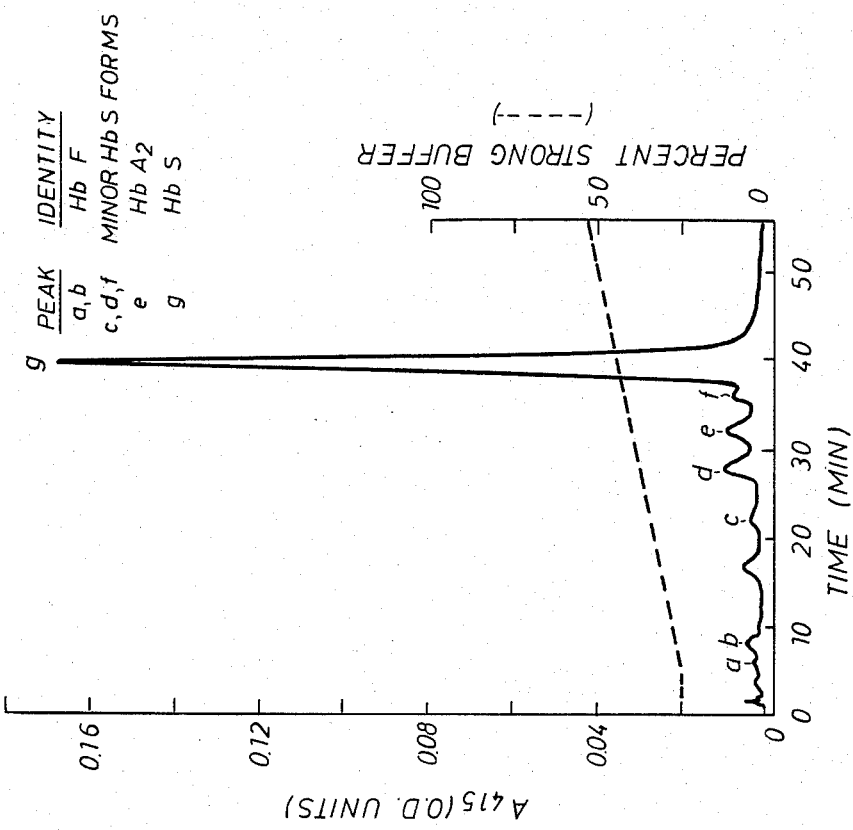
Fig. 10 SICKLE CELL ANEMIA HEMOGLOBIN
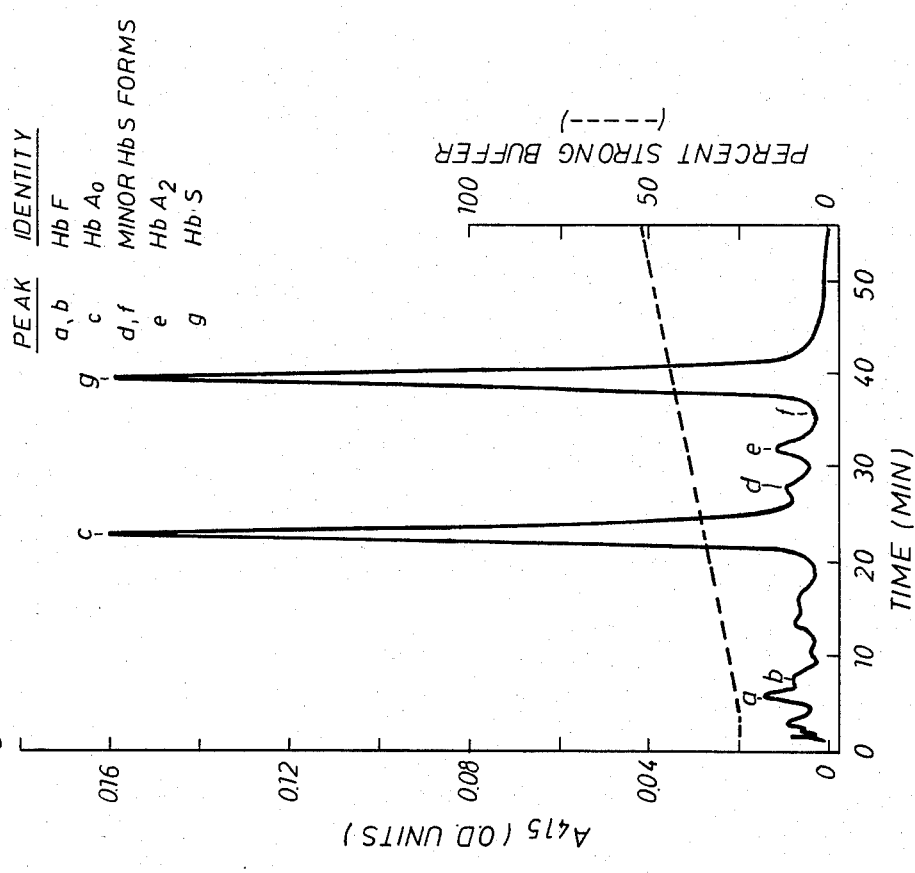
Fig. 9 HEMOGLOBIN S CARRIER

CHROMATOGRAPHIC SUPPORT MATERIAL

FIELD OF THE INVENTION

This invention is directed to a coated support material useful in liquid chromatography and to a method for producing the same. More particularly this invention is directed to a support material suitable for high performance liquid chromatography.

BACKGROUND OF THE INVENTION

Ion-exchange is one of the most useful techniques available for resolving protein mixtures. Most proteins have isoelectric points below 6 and therefore anion-exchange is more generally useful than cation-exchange. There are, however, a number of protein mixtures which are best resolved by cation-exchange.

The most widely used materials for protein cation-exchange have been cellulose or dextrans containing carboxymethyl groups. These materials exhibit the general requirements of hydrophilicity and high capacity which is necessary for general protein chromatography.

Recent advances in chromatography involving the use of finer column packings with high surface areas have led to a technique known as high performance liquid chromatography (HPLC). In modern HPLC, pressures of several thousand lb/in$^2$ are often developed within the chromatography columns. This requires that the column packing materials be rigid and non-collapsible. The carbohydrate base materials used in protein cation-exchange heretofore are not suitable for use in HPLC as they cannot withstand the high pressures involved. To achieve materials meeting this requirements, porous inorganic materials, such as silica and alumina have heretofore been utilized as the support material with organic stationary phases on the surface to obtain a variety of liquid chromatography column packing materials. Recently, hydrophilic organic supports have been developed for this purpose, but the pressure limit of these packings is still appreciably lower than that of the inorganic base materials and their application is therefore limited. In addition these materials are not available in the wide range of pore and particle diameters that the inorganic support materials are.

Requirements for an inorganic support which is to be used for protein HPLC are that the material be microparticulate, hydrophilic and macroporous. An anion-exchange material is available which meets these requirements, but until recently no such cation-exchange materials were available. Glass is naturally anionic, and porous glass beads have been used for cation-exchange of proteins. Glass, however, is not an entirely acceptable material as it binds many proteins irreversibly. The cation exchange is best carried out through anionic groups in a hydrophilic, organic coating on the surface of the inorganic support. Such material is described in U.S. Pat. No. 4,108,603, to Chang et al. This material suffers several drawbacks in that it requires several steps to prepare and is difficult to reproduce. A more promising coating, based on polyethyleneimine-diglycolic anhydride, has been developed and support materials based on this material are commercially available.

Studies have shown the advantages of using short polymers to prepare coatings for inorganic chromatography supports. A polymer that reacts well with the support surface and not with itself will form a self-assembling coating. Such a coating is reproducible and covers the inorganic surface uniformly. The coating also tends not to fill in pores or to cement the inorganic particles together. The present invention produces a self-assembling coating which is highly reproducible and which meets the requirements of high performance liquid chromatography.

SUMMARY OF THE INVENTION

The invention provides a method for producing a coated support material. The method comprises providing a substrate having surface amine functional groups and contacting the substrate with a polymer having succinimide units under conditions which promote the reaction of the polymer with the amine groups and the substrate. The polymer may be derivatized before or after reacting with the substrate to provide a variety of chromatographic support materials. The invention also provides a support material comprised of a substrate coated with a polymer having succinimide units or derivatives of those units.

BRIEF DESCRIPTION OF THE DRAWINGS

FIG. 7 is the cation-exchange chromatography of an AFSC hemoglobin standard. Sample: 25 μl of standard AFSC solution diluted 14-fold. Elution: 32 min. linear gradient, 22–100% strong buffer. Detection: $A_{415}=0.2$ a.u.f.s. Other conditions: same as FIG. 6.

FIG. 8 is a normal hemoglobin profile. Sample 25 μl of hemoglobin solution diluted 37-fold. Elution: 140 min. linear gradient, 25–100% strong buffer. Other conditions: same as FIG. 7.

FIG. 9 is a hemoglobin profile from an individual heterozygous for sickle-cell trait. Sample: 25 μl of hemoglobin solution diluted 23-fold. Conditions: see FIG. 8.

FIG. 10 is a hemoglobin profile from an individual homozygous for sickle-cell trait. Sample: 25 μl of hemoglobin solution diluted 34-fold. Conditions: see FIG. 8.

GENERAL DESCRIPTION

Figure 1:
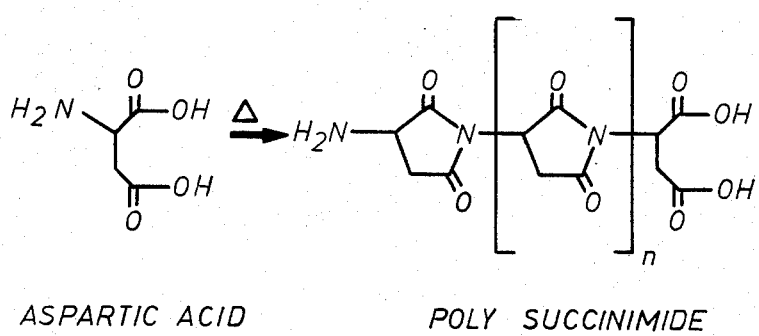
FIG. 1 demonstrates the conversion of aspartic acid to polysuccinimide.

The present invention is a self-assembling coating which converts a substrate into a support material for use in liquid chromatography. The invention is particularly advantageous when used to produce a cation-exchange material for proteins. The support material is prepared by coating the substrate with a polymer containing succinimide (anhydroaspartic acid) units. The succinimide units can be hydrolyzed to produce a cation-exchange material for proteins or otherwise derivatized to produce support materials having utility in other various techniques of liquid chromatography.

Polysuccinimide (polyanhydroaspartic acid) is an ideal material for a cation-exchange coating. Polysuccinimide can be immobilied on a surface through reaction with surface amino groups. Alternatively a coupling agent such as an amino-silane may first be reacted with the polymer and that reaction product reacted with the substrate. However, it is preferable to first react the coupling agent with the substrate. As a potential cation-exchange group is part of the polysuccinimide no additional reaction is needed to produce a cation-exchange material. This characteristic of the material promotes reproducibility. Thus, hydrolysis of the residual succinimide groups in the polymer produces immobilized polyaspartic acid. This coating is useful for protein chromatography as it contains many carboxylic acid groups in a hydrophilic polypeptide matrix.

Immobilized polyaspartic acid shows great potential as a cation-exchange material for the HPLC of proteins. Preparation of the support material is simple and materials of high quality may be uniformly reproduced. Columns packed with the material feature excellent performance in terms of capacity, selectivity, recovery of enzyme activity and peak shape.

The organic coating is attached to the substrate through the use of a reactive coupling agent. Suitable inorganic substrates include those made of glass, silica, alumina and titania. Organic substrates are also viable options. Materials such as polystyrene, polymethacrylates and polyacrylates may be used. The coupling agent in the case of an inorganic substrate will typically be an amino-silane. However, any material capable of bonding both with the substrate and with the organic coating can be used for this purpose. A typical example of a suitable coupling agent is 3-aminopropyltriethoxysilane.

Polyaspartic acid is probably attached to the substrate surface at several points per molecule. This would be an "island" type of coating, as the individual polymer molecules are not cross-linked into a continuous network. Nonetheless, the surface seems to be uniformly covered and the coating is quite durable. The high ion-exchange capacity of the coating and its ready release of adsorbed proteins may be ascribed to its hydrophilic, polypeptide nature and to the location of ionized groups on branch ends removed from the solid surface. Such "fuzzy" coatings have a high surface area and function well in the chromatography of proteins. The hemoglobin ion-exchange capacity (IEC) is several times higher than that of the polyethyleneimine-diglycolic anhydride material referred to above. This is possibly accounted for by long threads of polyaspartic acid projecting from the surface of the substrate well into the center of the pores. This structure would possess a much higher surface area than other more surface oriented coatings.

The polyaspartic acid coating may be placed on the inorganic substrate in a batch operation or alternatively it may be generated in situ by circulating the solution of polysuccinimide through a column of inorganic substrate previously treated with a coupling agent. In either case, the polyaspartic acid is produced by treatment of immobilized polysuccinimide with a hydrolyzing solution. In the case of in situ generation the solution is circulated through the column. Examples of both manners of preparation will follow. It has been found that columns prepared with the in situ generated coating exhibit slightly lower capacity and resolution than columns packed with materials prepared batchwise.

Polysuccinimide can be used to prepare a variety of chromatography supports in addition to the cation exchanger. The reactivity of polysuccinimide-silica offers a convenient route to derivatives other than polyaspartic acid-silica. The neutral, zwitterionic poly-2-aminoethylaspartamide-silica, for example may be useful for steric exclusion chromatography. Such derivatives are easily prepared as amines add readily in N,N-dimethylformamide (DMF) solution to yield poly-alpha,beta-D,L-aspartamides. Amine containing compounds can be reacted with the succinimide residues either before or after immobilization. In the case of small molecules, reaction before immobilization yields more reproducible products. Reaction after immobilization affords a means of immobilizing enzymes on a polypeptide matrix. Various ligands can also be added to the polysuccinimide coating to convert it into a material useful in affinity chromatography. The polypeptide nature of the coating would favor good performance in this application. One problem with this material is the seemingly unavoidable presence of some aspartyl groups in the coating. The effect of these groups may possibly be neutralized by adding ethylenediamine to the coating along with the affinity ligand or enzyme.

Incorporation of sulfonate or phosphonate groups into the polysuccinimide coating produces strong cation-exchange materials. This can be accomplished by reacting 2-amino-ethylphosphonic acid or taurine with the immobilized polysuccinimide. Incorporation of other groups would yield materials that might be useful in chromatofocusing.

FIG. 1 illustrates the conversion of aspartic acid to polysuccinimide. Polysuccinimide is formed in almost quantitative yields by heating aspartic acid under conditions which cause it to condense.

Figure 2:
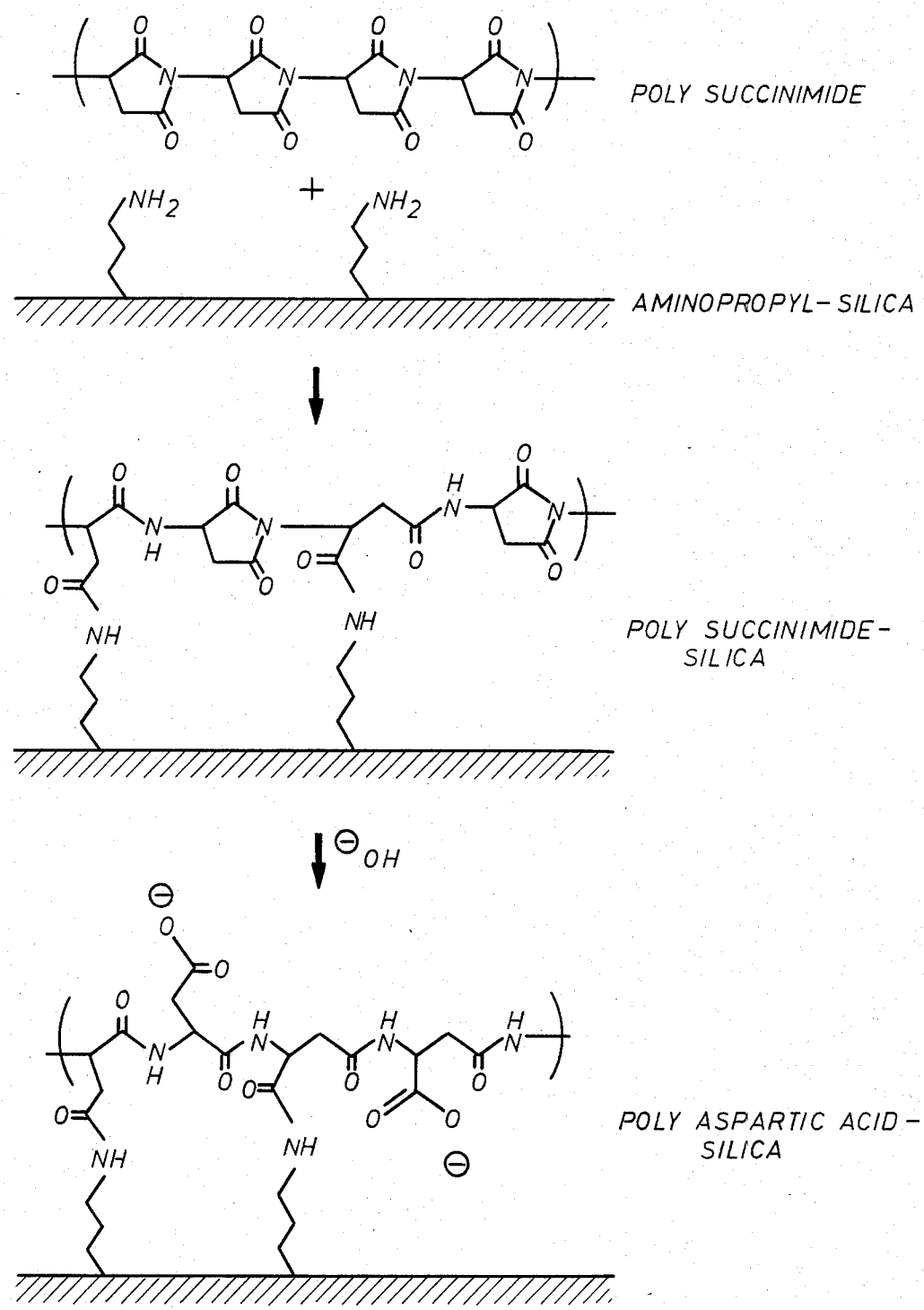
FIG. 2 shows the reaction of polysuccinimide with aminopropyl silica and the subsequent hydrolysis of residual succinimide units.

FIG. 2 illustrates the method used to prepare polyaspartic acid-silica. A microparticulate silica gel was selected which had pores wide enough to give most proteins free access to the pore interior. The silica was given a covalently bonded coating of aminopropyl groups. Polysuccinimide was then reacted with the amino groups. This produced a polysuccinimide-silica in which the polymer was immobilized through amide bonds to the surface. Subsequent treatment with base catalyzed the hydrolysis of unreacted succinimide rings, producing the polyaspartic acid coating.

EXAMPLES

Preparation of Aminopropyl-silica 4.0 grams of Vydac silica was weighed into a large test tube and covered with 30 ml of a 5% solution (w/v) of 3-aminopropyltriethoxysilane in toluene. The mixture was mixed on a vortex generator and then put under vacuum (with a one hole stopper connected to a small pump) for 30 seconds to remove air from the pores of the silica. The mixture was heated for two hours in a boiling water bath with occasional swirling. The product was collected in a medium pore sintered glass funnel and washed well with toluene and acetone and then dried by continued suction.

Preparation of Polysuccinimide 50 grams (0.38 mole) of D,L-aspartic acid was placed in a thin layer in a crystallization dish and heated in an oven at 190° C. for 50 hours. The resulting light tan powder weighed 37.9 grams (indicating virtually quantitative dehydration, assuming a unit molecular weight of 97 for the product). The powder dissolved with heating in 150 ml of DFM except for a small amount of white material. This material was centrifuged out, leaving a brown solution. The polysuccinimide was collected by pouring the DMF solution into four volumes of diethyl ether with rapid stirring and collecting the precipitated product by centrifugation. It is also possible to precipitate the polysuccinimide by using water in place of diethyl ether. The precipitate was freed of DMF by shaking several times with the precipitating solvent followed by resedimentation. The precipitate was then lyophilized to yield a light tan powder, completely soluble in DMF. The molecular weight of this product has been reported to be approximately 13,000. Although the use of either water or ether yields an acceptable product for the purposes of this invention, the precipitate settles more rapidly from ether and its use also precludes the possible hydrolysis of some of the succinimide rings.

Preparation of Polysuccinimide-silica 4.0 grams of aminopropyl-silica was vortexed and degassed as above in 20 ml of a 5% solution (w/v) of polysuccinimide in DMF. The mixture was left 24 hours at room temperature with occasional swirling. The tan colored product was collected in a funnel and washed with DMF and acetone.

Figure 3:
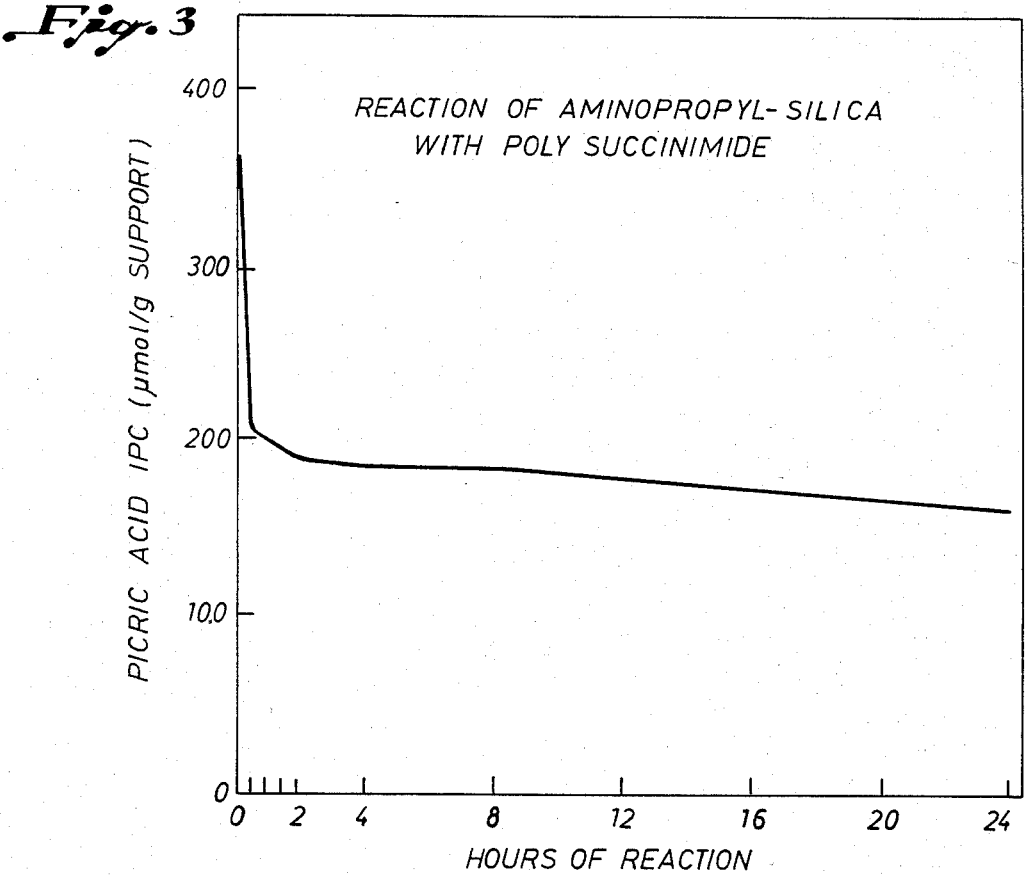
FIG. 3 shows the rate of reaction of polysuccinimide with aminopropyl-silica as determined by ion-pairing capacity with picric acid.

The reaction of polysuccinimide with surface aminopropyl groups causes free amino groups to disappear. The rate of disappearance can be measured with the picric acid assay. This assay permits the quantification of accessible amine groups on a solid surface through the reversible formation of ion-pairs with picric acid. Details of this assay are described in the *Journal of Chromatography*, 185 (1979) 375–392. Samples of aminopropyl-silica were immersed in a 5% solution of polysuccinimide and worked up for the assay at various times in order to optimize reaction time. FIG. 3 shows that the reaction is almost complete within 0.5 hours. A thorough coating of the surface can be achieved by letting the reaction progress for 24 hours.

Figure 4:
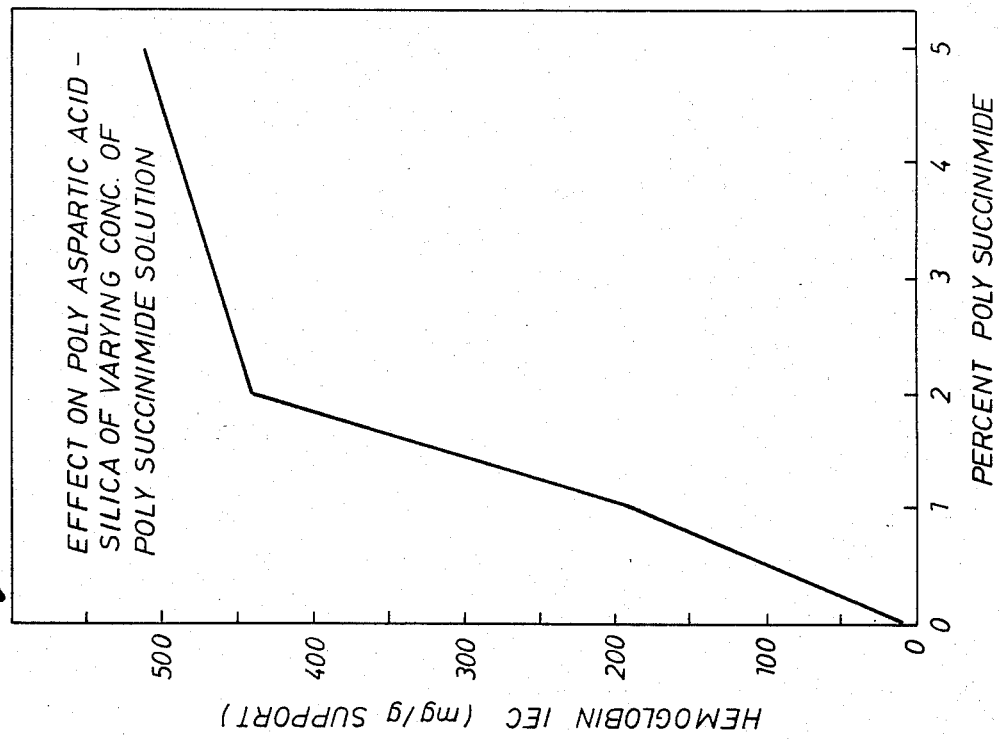
FIG. 4 shows the effect on the quality of polyaspartic acid-silica materials prepared from different concentrations of polysuccinimide solutions as measured by hemoglobin ion-exchange capacity.

The concentration of the polysuccinimide solution to be used in the reaction with the aminopropyl-silica was also optimized. Solutions of several concentrations were used to prepare polysuccinimide-silica in 24-hour reactions and the products hydrolyzed to polyaspartic acid silica as described below. The ion-exchange capacity (IEC) for hemoglobin was used to relate the properties of the product to the quality of the polysuccinimide coatings. FIG. 4 shows there is an appreciable difference in the coatings when the polysuccinimide concentration is raised from 1 to 2%, but little difference when the concentration is raised from 2 to 5%. Therefore, a 5% solution is suitable for producing a reproducible coating in a relatively short time.

Preparation of Polyaspartic Acid-Silica 4.0 grams of polysuccinimide-silica was vortexed and degassed as above in a solution containing 15 ml DMF, 10 ml water, 0.825 grams (9.3 mmol) beta-alanine and 0.625 ml (4.5 mmols) triethylamine. The mixture was left 24 hours at room temperature with occasional swirling. This treatment removed much of the material's former tan color. The light tan product was collected in a funnel and washed with water, 0.05M HCl, water and acetone. The product was then dried by continued suction.

It has been reported that beta-alanine reacts with polysuccinimide to give poly-2-carboxyethylaspartamide. The subsequent hydrolysis of unreacted succinimide residues is catalyzed with base triethylamine. This reaction has been investigated as a possible route to a cation exchange material. Table 1 shows the hemoglobin IEC of several such products prepared from polysuccinimide-silica. Reaction of beta-alanine with succinimide residues is far slower than their hydrolysis in the presence of triethylamine; thus the coatings prepared here are primarily polyaspartic acid and not poly-2-carboxyethylaspartamide. The inclusion of beta-alanine in the triethylamine solution gives a product with a slightly higher IEC and therefore beta-alanine is routinely added to the hydrolysis solution. It is evident from Table 1 that there is slow hydrolysis of the coating in the absence of a catalyst; this hydrolysis is slower in DMF/water than in water alone. However, catalyzed hydrolysis is faster in DMF/water solutions. As seen in Table 1, untreated polysuccinimide-silica has a modest hemoglobin IEC. This may reflect the presence of aspartyl-groups in the middle of the polymer as well as at the C-terminus.

TABLE I

EFFECT OF ADDITIVES ON CATION-EXCHANGE MATERIALS PRODUCED FROM POLYSUCCINIMIDE-SILICA 120-mg portions of polysuccinimide-Vydac were vortexed and degassed in 4.4 ml of solvent. The solvent was water or 2.6 ml DMF + 1.8 ml water. 147 mg. of beta-alanine and/or 111 mg triethylamine were present in the solvent as noted. Mixtures were left 15 hours at room temp with occasional vortexing. The products were filtered and washed as with polyaspartic acid-silica (see Examples).

| Solvent | beta-Alanine | Triethylamine | Hemoglobin IEC (mg/g support) |
|---|---|---|---|
| DMF + Water | + | + | 382 |
|  | + | − | 95 |
|  | − | + | 365 |
|  | − | − | 84 |
| Water | + | + | 370 |
|  | + | − | 158 |
|  | − | + | 305 |
|  | − | − | 170 |

Hydrolysis of a polysuccinimide coating to a polyaspartic acid coating generates numerous carboxylic acid groups. In order to determine the time needed for hydrolysis it is helpful to know the concentration of these carboxylic acid groups. Unfortunately, there is no assay which can quantitate carboxyl groups conveniently in the manner that the picric acid assay quantitates amine groups. The native silanol groups of silica interfere with the quantitation of carboxyls by aqueous titration.

The concentration of carboxyl groups in the coating can be estimated by indirect methods. The reaction of polysuccinimide-silica with ethylenediamine produces a coating containing aminoethyl groups. These can be quantitated with the picric acid assay. The monohydrochloride of ethylenediamine was used to promote reaction with only one amine residue and not both (which would simply crosslink the coating through amide bonds and leave the picric acid ion-pairing capacity (IPC) unchanged).

Figure 5:
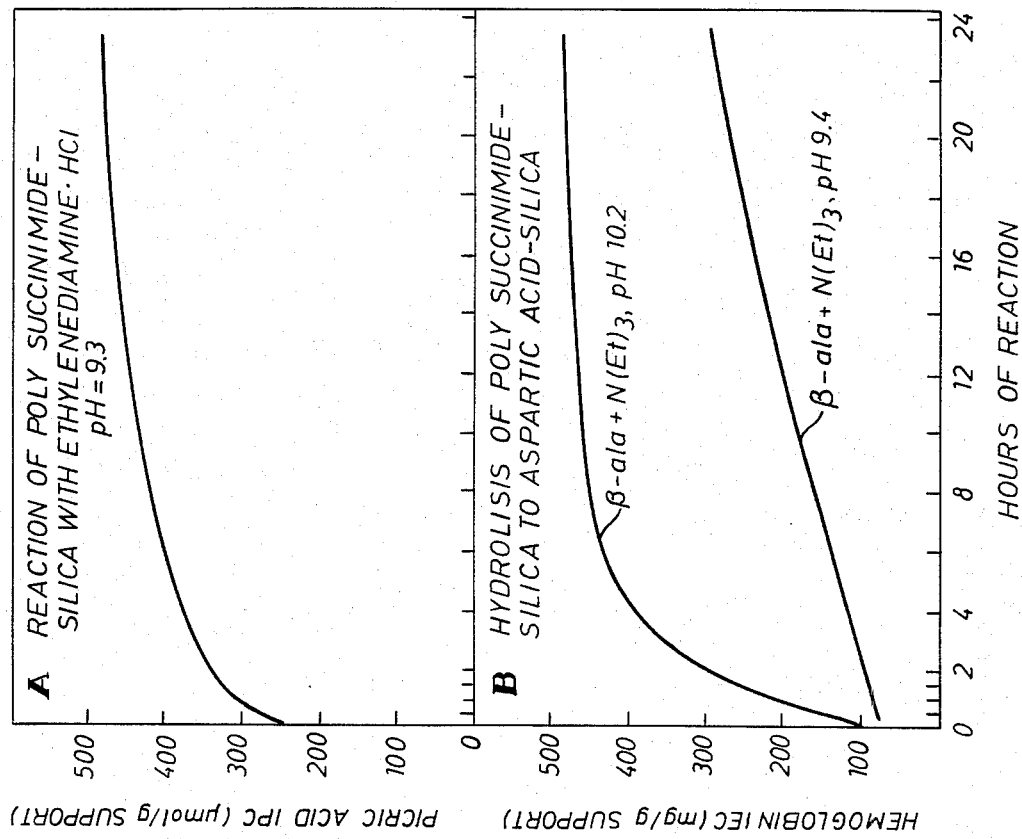
FIG. 5A shows the rate of reaction of polysuccinimide-silica with ethylenediamine.
FIG. 5B shows the rate of hydrolysis of polysuccinimide-silica to polyaspartic acid-silica.

FIG. 5A shows the course of the reaction versus time. The reaction is almost complete after 24 hours, with 0.26 mmols of ethylenediamine added per gram of polysuccinimide-silica. This constitutes a lower limit for the concentration of hydrolyzable succinimide residues, as this method would not measure the following types of residues:

(a) Residues involved in a crosslinking reaction with ethylenediamine and not end-on addition;

(b) Aspartyl groups present before the reaction;

(c) Residues whose hydrolysis to aspartyl groups was catalyzed by the basic ethylenediamine.

The product, poly 2-aminoethylaspartamide-silica has almost no hemoglobin IEC (see Table 2 below). This indicates that there are enough carboxyl groups in the coating to the give the product a neutral zwitterionic character. The concentration of carboxyl groups in polyaspartic acid-silica is probably about 0.4 mmol/g material. This is approximately the same concentration of ion-exchange sites present in an anion-exchange material based on Vydac TP (the silica used here) with a monolayer coating of polyethyleneimine. This indicates that the polyaspartic acid coating is quite thin.

The rate of coating hydrolysis can be followed by a second indirect method, the increase in the hemoglobin IEC as hydrolysis proceeds. FIG. 5B shows the time course of hydrolysis with two different concentrations of triethylamine in the hydrolysis solution. The rates differ by a factor of 8 and are directly proportional to the difference in the concentration of hydroxyl groups in solution. At the higher pH, hydrolysis seems to be complete in 24 hours. However, a study with an anion-exchange silica showed that the hemoglobin IEC leveled off once the surface ion-exchange sites reached a certain concentration and was little affected by any additional increase. Thus, the rate of hydrolysis could be slower than that indicated in FIG. 5B. On the other hand, prolonged exposure to base could cause dissolution of the silica. Therefore, hydrolysis for 24 hours seems to be a reasonable compromise between the requirements of reaction completeness and support integrity.

Derivatives of Polysuccinimide-Silica

The reactivity of polysuccinimide-silica permits a variety of functional groups to be incorporated into the coating. Table 2 shows the ion-exchange properties of the products of reaction with ethanolamine (prepared as with ethylenediamine hydrochloride as described below), ethylenediamine hydrochloride, and Polyethyleneimine 6 (PEI 6; a polyethyleneimine of approximately 600 molecular weight). The poly PEI aspartamide-silica is an anion exchanger for both small molecules and proteins; the ion-exchange capacity (IEC) for hemoglobin is only 58% of the IEC of the anion-exchange silica with a pellicular coating of PEI. This may reflect the presence of carboxyl groups in the coating. Similarly, poly 2-hydroxyethylaspartamide-silica which should be neutral has an appreciable hemoglobin cation-exchange capacity. Poly 2-aminoethylaspartamide-silica seems to have enough amino groups to balance the carboxyl groups and yield a neutral, zwitterionic coating, as discussed above.

TABLE 2

DERIVATIVES OF POLYSUCCINIMIDE-SILICA
Products were prepared as described above.

| Derivative | Hemoglobin Cation IEC (mg/g support) | Hemoglobin Anion IEC (mg/g support) | Picric Acid IPC (mmol/g support) |
|---|---|---|---|
| Poly 2-hydroxyethyl aspartamide-Vydac | 150 | 1 | 0.23 |
| Poly 2-aminoethyl aspartamide-Vydac | 8 | 3 | 0.44 |
| Poly PEI aspartamide-Vydac | 3 | 19 | 0.72 |

An alternative method of adding functional groups to the support material is to incorporate them into the polysuccinimide prior to its immobilization. This in some instances will yield products which are more reproducible than if incorporation were after immobilization. Prederivatization must not crosslink the polymer and must leave enough free succinimide residues to permit immobilization. This method was examined with the incorporation of the additive ethanolamine and Tris (hydroxylmethyl)aminomethane (Tris) into polysuccinimide. The resulting polymers contain some neutral, hydrophilic residues generated at the expense of potential anionic residues. Table 3 shows the IEC of polyaspartic acid-silica made with these derivatized polymers. As would be expected, the additives decrease the hemoglobin IEC, although the effect was less pronounced above the 5% additive level. Procedures for the preparation of these derivatives are given below.

TABLE 3

PRODUCTS MADE WITH POLYSUCCINIMIDE DERIVATIVES

| Additive | None | Ethanolamine | | Tris | |
|---|---|---|---|---|---|
| % Additive | 0 | 5 | 10 | 5 | 10 | 20 |
| Hemoglobin Cation IEC (mg/g support) | 487 | 349 | 345 | 351 | 325 | 325 |

Poly 2-aminoethylaspartamide-silica was prepared using the same procedure as for polyaspartic acid-silica except that the solution consisted of 0.25 ml (3.7 mmol) ethylenediamine, 0.50 g (3.7 mmol) ethylenediamine dihydrochloride, 20 ml DMF and 4 ml water. The product was washed with a saturated aqueous solution of triethylamine instead of 0.05M HCL.

Poly PEI aspartamide-silica was prepared using the same procedure as for polyaspartic acid except that the solution consisted of a 5% (w/v) solution of PEI 6 in a one to one DMF:water solvent. The mixture was allowed to react for 46 hours and the product was washed with a saturated aqueous solution of triethylamine instead of 0.05M HCl.

To exemplify the derivatization of polysuccinimide prior to its immobilization, ethanolamine and Tris were each dissolved in 2.5 ml DMF to produce solutions containing 0, 5, 10 and 20% of the molar equivalent of succinimide residues. Both the polysuccinimide solution and the additive solutions were cooled to 5° C. The additive solutions were then dropped into the vortexed polysuccinimide solutions and left 3 hours at room temperature. The solutions darkened almost immediately in proportion to the amount of additive present. The solution with no additive received 2.5 ml of DMF alone. 140 mg samples of aminopropyl-Vydac were each degased and vortexed in one of the solutions of derivatized polysuccinimide. They were left for 24 hours at room temperature with vortexing after 12 hours. The intermediate product was then filtered and washed with DMF and acetone and then dried by continued suction. Residual succinimide residues were hydrolyzed with beta-alanine and triethylamine solution as described above in the preparation of polyaspartic acid-silica.

APPLICATIONS

Figure 6:
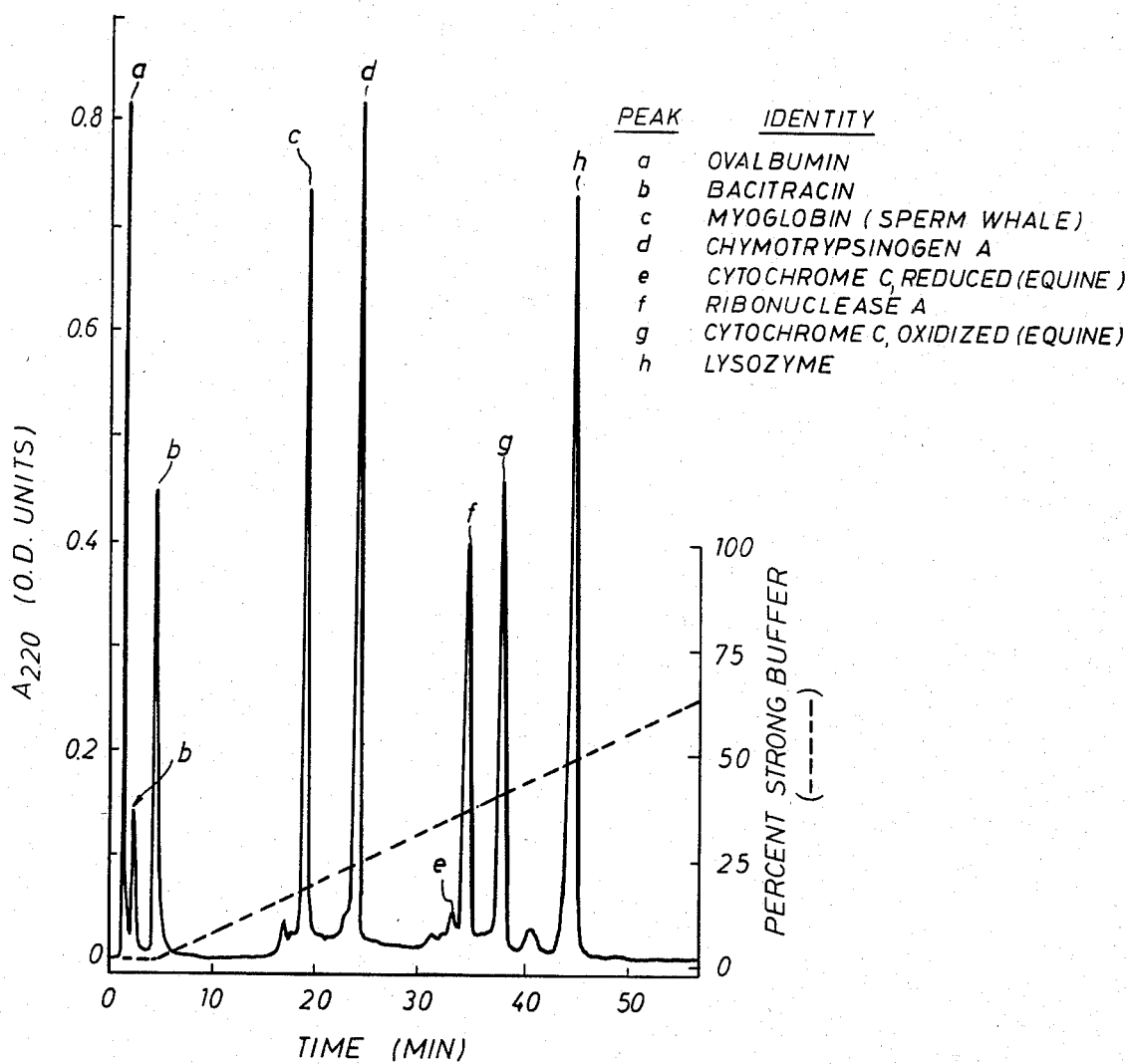
FIG. 6 shows the cation-exchange chromatography of protein standards. Column: polyaspartic acid-Vydac (10 micron), 20×0.46 cm. Sample: 25 μl containing 12.5 μg of ovalbumin and 25 μg each of the other proteins in the weak buffer. Flow rate: 1 ml/min. Elution: 80 min. linear gradient 0–100% strong buffer. Detection: $A_{220}=1.0$ a.u.f.s.

Protein mixtures are well resolved on polyaspartic acid-silica columns using gradients similar to those employed with carboxymethyl-type materials. The columns display high capacity and selectivity. FIG. 6 shows the separation of several standard proteins with isoelectric points ranging from 4.7 to over 11. Peaks are sharp and show minimal tailing.

Clinical hemoglobin samples are frequently analyzed with cation-exchange columns. Polyaspartic acid-silica functions especially well in this application. FIG. 7 is the profile of an AFSC hemoglobin standard. FIG. 8 is a normal hemoglobin profile, generated using a shallower gradient than with FIG. 7. FIGS. 9 and 10 are the hemoglobin profiles of individuals who are heterozygous and homozygous, respectively, for sickle cell trait. Excellent selectivity is observed in the region of hemoglobins $A_0$, $A_2$ and S and even better resolution is obtained if a column of 5 micron packing is used. This is important for the resolution of some mutant hemoglobin forms of clinical significance. For example, hemoglobins E and $A_2$ have not been resolved with other ion-exchange materials but are resolved on polyaspartic acid-silica.

The polyaspartic acid coating is quite stable. Columns last for hundreds of hours of use with no decrease in efficiency or capacity. In some cases, a column's retention of proteins increases by up to 5% during the first 100 hours of operation. This could reflect ongoing hydrolysis of residual succinimide residues. Alternatively, there could be a reorientation of branch ends toward the outside of the coating, increasing its surface area. This process is hastened by eluting the column with a strong buffer solution for several hours.

Polyaspartic acid-silica columns exhibit a high recovery of enzyme activity. Several enzymes were applied to a polyaspartic acid-silica column and eluted with a gradient similar to those used with carboxymethyl-cellulose. Adenylosuccinate synthetase, thiolase I, and beta-hydroxyacyl-CoA dehydrogenase were eluted with quantitative recovery of applied activity. This high recovery may reflect the polypeptide nature of the coating, which makes it suited for interaction with enzymes without causing denaturization.

The foregoing invention has been exemplified by specific embodiments with no intent to limit the scope of the invention thereto. Modifications and variations of the invention will be apparent to those skilled in the art. Applicant intends that the following claims cover all such equivalent modifications and variations as fall within the true spirit and scope of the invention.

What is claimed is:

1. A coated support material comprising a chromatographically suitable substrate; and an uniform immobilized coating, susceptible to derivatization to a form suitable for protein chromatography, on said substrate formed by the reaction of a polymer containing succinimide units with said substrate.

2. The support material of claim 1 wherein succinimide units of said immobilized polymer are converted to aspartyl residues thereby producing a hydrophilic coating.

3. The support material of claim 1 wherein succinimide units of said immobilized polymer are converted to aspartamides.

4. The support material of claim 2 or 3 wherein said polymer is polysuccinimide.

5. The support material of claim 2 or 3 wherein said polymer is a derivative of polysuccinimide.

6. The support material of claim 2 or 3 wherein said polymer is a copolymer containing succinimide units.

7. The support material of claim 2 or 3 wherein said substrate is a porous inorganic support material selected from the group consisting of glass, alumina, silica and titania.

8. The support material of claim 7 wherein said substrate consists of particles of about 5 to about 10 microns in diameter.

9. The support material of claim 1 wherein said substrate is an organic material chosen from the group consisting of polystyrene, polyacrylates and polymethacrylates.

10. A coated support material comprising a chromatographically suitable substrate; and a uniform immobilized coating, susceptible to derivatization to a form suitable for protein chromatography, on said substrate formed by the reaction of polysuccinimide with said substrate.

11. The support material of claim 10 wherein succinimide unit of the immobilized polysuccinimides are converted to aspartyl residues thereby producing a hydrophilic coating.

12. The support material of claim 10 wherein succinimide units of the immobilized polysuccinimide are converted to aspartamides.

13. The support material of claim 11 or 12 wherein said substrate is a porous inorganic support material selected from the group consisting of glass, alumina, silica and titania.

14. The support material of claim 13 wherein said substrate consists of particles of about 5 to about 10 microns in diameter.

15. The support material of claim 11 or 12 wherein said substrate is an organic material chosen from the group consisting of polystyrene, polyacrylates and polymethacrylates.

16. A coated support material comprising a chromatographically suitable inorganic substrate material; and an immobilized coating on said substrate formed by the reaction of polysuccinimide with said substrate and the subsequent conversion of succinimide units of the polysuccinimide to aspartyl residues.

17. The support material of claim 8 wherein said substrate material is selected from the group consisting of glass, alumina, silica and titania.

18. The support material of claim 8 wherein said substrate consists of particles of about 5 to about 10 microns in diameter.

19. A method for producing a coating on a substrate, said method comprising:
providing a chromatographically suitable substrate material having surface amine functional groups, said amine groups being primary amines, secondary amines or both;
contacting said substrate material with a polymer having succinimide units under conditions which promote the reaction of said polymer with said amine groups of said substrate thereby immobilizing said polymer on said substrate and forming a uniform coating susceptible to derivatization to a form suitable for protein chromatography.

20. The method of claim 19 wherein said polymer is polysuccinimide.

21. The method of claim 19 wherein said polymer is a derivative of polysuccinimide.

22. The method of claim 19 wherein said polymer is a copolymer containing succinimide units.

23. The method of claim 19 which further comprises converting said succinimide units in the immobilized polymer to aspartyl residues thereby producing a hydrophilic coating.

24. The method of claim 19 which further comprises reacting succinimide units in the immobilized polymer with a substance containing one or more primary or secondary amine functional groups.

25. The method of claim 19 which further comprises reacting succinimide units in the immobilized polymer to introduce phosphonate and sulfonate groups.

26. The method of claim 19 wherein said substrate material is an inorganic substrate provided from the group consisting of silica, glass, alumina and titania.

27. The method of claim 19 wherein said polymer is immobilized on said substrate in a batchwise preparation.

28. The process of claim 19 wherein said substrate material is packed into a column and reacted in situ with said polymer.

29. A method for producing a coating on a substrate, said method comprising:
providing a chromatographically suitable substrate material; and
contacting said substrate material with a polymer having succinimide units and having functional groups capable of reacting with said substrate material under conditions which promote the reaction of said functional groups with said substrate material so as to form an uniform immobilized coating susceptible to derivatization to a form suitable for protein chromatography.

30. A method for producing a hydrophilic coating on a substrate, said method comprising:
providing a chromatographically suitable substrate material having surface amine functional groups, said amine groups being primary amines, secondary amines, or both; and
contacting said substrate material with polysuccinimide under conditions which promote the reaction of said polysuccinimide with said amine groups of said substrate thereby immobilizing said polymer on said substrate and forming a uniform coating susceptible to derivatization to a form suitable for protein chromatography.

31. The method of claim 30 wherein said substrate material is an inorganic substrate provided from the group consisting of silica, glass, alumina and titania.

32. The method of claim 31 which further comprises converting succinimide units of said immobilized polysuccinimide to aspartyl residues thereby producing a hydrophilic coating.

33. The method of claim 31 which further comprises reacting succinimide units of said immobilized polysuccinimide with a substance containing one or more primary or secondary amine functional groups.

34. The method of claims 32 or 33 wherein said polymer is immobilized on said substrate in a batchwise preparation.

35. The method of claims 32 or 33 wherein said substrate material is packed into a column and reacted in situ with said polymer.

36. A method for producing a coating on a substrate, said method comprising:
providing a chromatographically suitable substrate material; and
contacting said substrate material with a polysuccinimide having functional groups capable of reacting with said substrate material under conditions which promote the reaction of said functional groups with said substrate material so as to form an uniform immobilized coating susceptible to derivatization to a form suitable for protein chromatography.

37. The method of claim 36 which further comprises converting succinimide units in said immobilized polysuccinimide to aspartyl residues thereby producing a hydrophilic coating.

38. The method of claim 36 which further comprises reacting succinimide units of said immobilized polysuccinimide with a substance containing one or more primary or secondary amine functional groups.

39. A method for producing a hydrophilic coating on a substrate, said method comprising:
providing a chromatagraphically suitable inorganic substrate material having surface amine functional groups, said amine groups being primary amines, secondary amines or both;
contacting said substrate material with polysuccinimide under conditions which promote the reaction of said polymer with said amine groups of said substrate thereby immobilizing said polymer on said substrate and forming a uniform coating susceptible to derivatization to a form suitable for protein chromatography; and
converting succinimide units in the immobilized polysuccinimide to aspartyl residues.

40. The method of claim 39 wherein said inorganic substrate material is provided from the group consisting of silica, glass, alumina and titania.

41. The method of claim 39 wherein said polymer is immobilized on said substrate in a batchwise preparation.

42. The process of claim 39 wherein said substrate material is packed into a column and reacted in situ with said polymer.

43. A method for producing a hydrophilic coating on a substrate, said method comprising:
providing a chromatographically suitable inorganic substrate material;
contacting said substrate material with polysuccinimide having functional groups capable of reacting with said substrate material under conditions which promote the reaction of said functional groups with said substrate material so as to form an uniform immobilized coating susceptible to derivatization to a form suitable for protein chromatography; and
converting succinimide units of said polysuccinimide to aspartyl residues.

* * * * *